US005849264A

United States Patent [19]

Bassam et al.

[11] Patent Number: 5,849,264

[45] Date of Patent: Dec. 15, 1998

[54] MICROENCAPSULATED AEROSOL INSECTICIDES

[75] Inventors: Dean Anthony Bassam, Georges Hall; Ian Andrew Thompson, Collaroy Plateau; Gavin Ian Allison, Clareville, all of Australia

[73] Assignee: R & C Products PTY Limited, Ermington, Australia

[21] Appl. No.: 727,779

[22] Filed: Oct. 8, 1996

[30] Foreign Application Priority Data

Oct. 10, 1995 [GB] United Kingdom .................. 9520705

[51] Int. Cl.[6] ............................ A01N 25/06; A01N 25/28

[52] U.S. Cl. ............................ 424/45; 424/406; 424/408; 514/962; 514/963

[58] Field of Search .............................. 424/45, 405, 406, 424/489, 408; 514/962, 963; 264/4, 4.1; 428/402.2

[56] References Cited

U.S. PATENT DOCUMENTS 5,631,014 5/1997 Ishida et al. ............................ 424/405

FOREIGN PATENT DOCUMENTS

| | | |
|---|---|---|
| B1-60 177/80 | 2/1981 | Australia . |
| B-85934/82 | 1/1983 | Australia . |
| 0 006 212 | 1/1980 | European Pat. Off. . |
| 0 006 212 A1 | 1/1980 | European Pat. Off. . |
| 1107140 | 3/1968 | United Kingdom . |
| WO 96/02136 | 2/1996 | WIPO . |
| WO 96/02136 A1 | 2/1996 | WIPO . |

OTHER PUBLICATIONS

Chem.Abs. 98:84902e vol. 98, No. 11, 1983.

*Primary Examiner*—Neil S. Levy
*Attorney, Agent, or Firm*—Fish & Richardson P.C.

[57] ABSTRACT

An insecticidal composition in the form of an aerosol water-in-oil emulsion is disclosed which comprises:

(a) an amount of an aqueous suspension of microencapsulated insecticide to give an insecticide concentration in the composition of from 0.001 to 5% w/w;
(b) one or more solvents in an amount of from 1 to 20% w/w;
(c) one or more emulsifiers in an amount of from 0.2 to 10% w/w and selected from the group comprising mono-, di-and tri-sorbitan esters, polyoxyethylene sorbitan esters, mono- and poly-glycerol esters, ethoxylated nonionic emulsifiers, propoxylated nonionic emulsifiers and ethoxylated/propoxylated nonionic emulsifiers;
(d) from 2 to 80% w/w of one or more propellants;
(e) optionally from 0.001 to 5% w/w of one or more oil phase soluble insecticides; and
(f) the balance being water.

39 Claims, No Drawings

MICROENCAPSULATED AEROSOL INSECTICIDES

FIELD OF THE INVENTION

This invention relates to insecticidal compositions in aerosol form, in particular to such compositions where the insecticidally active ingredients are microencapsulated so as to provide a sustained release effect.

BACKGROUND OF THE INVENTION

It is well recognised in the art that microencapsulation of insecticides is useful where it is desired to provide compositions where the insecticide is subject to sustained release. The advantage of such compositions is obvious in that an insecticidal effect is provided over a prolonged period of time.

Such compositions may, for example, be used in and around buildings so as to prevent the entry of insects.

A variety of microencapsulation methods and compositions are known in the art as represented by the microencapsulated lambda-cyhalothrin (available from Zeneca as DEMAND CS®). This material is available as 2.5 and 10% w/v aqueous capsule suspensions. In use, it is diluted with water and dispensed using a suitable spray means.

Whilst such diluted formulations are useful for professional pest controllers, they are of limited use owing to the inconvenience of preparation, particularly in domestic or other situations where ready to use non-sustained release insecticidal formulations are currently available. There is, therefore, a strong requirement for a sustained release ready to use formulation suitable for domestic and other situations.

One form of insecticide composition that is widely used domestically are aerosol insecticides. Generally water based aerosol insecticide compositions are emulsions with the active insecticide(s) being incorporated in the continuous oil phase.

By contrast, incorporation of microencapsulated insecticides, particularly microencapsulated insecticides that are aqueous dispersions or suspensions into aerosol compositions has been found to be problematic owing to the instability of the so-formed emulsions. This instability has been attributed to the fact that the microencapsulated insecticide is present in the dispersed aqueous phase rather than the oil phase as occurs with conventional water based aerosol insecticides.

Given the potential utility of sustained release insecticides in aerosol form, the present inventors have directed considerable efforts towards providing a formulation which is both effective and stable.

Surprisingly, the present inventors have found that it is possible to produce such formulations by using particular emulsifiers that act to stabilise the compositions whilst not impairing insecticidal effectiveness.

BRIEF SUMMARY OF THE INVENTION

Accordingly, the present invention consists in an insecticidal composition in the form of an aerosol water-in-oil emulsion comprising:

(a) an amount of an aqueous suspension of microencapsulated insecticide to give an insecticide concentration in the composition of from 0.001 to 5% w/w;
(b) one or more solvents in an amount of from 1 to 20% w/w;
(c) one or more emulsifiers in an amount of from 0.2 to 10% w/w and selected from the group comprising mono-di-and tri-sorbitan esters, polyoxyethylene sorbitan esters, mono- and poly-glycerol esters, ethoxylated nonionic emulsifiers, propoxylated nonionic emulsifiers and ethoxylated/propoxylated nonionic emulsifiers;
(d) from 2 to 80% w/w of one or more propellants;
(e) optionally from 0.001 to 5% w/w of one or more oil phase soluble insecticides; and
(f) the balance being water.

In a second and related aspect, the present invention further consists in an insecticidal composition in the form of an aerosol water-in-oil emulsion comprising:

(a) an amount of an aqueous suspension of microencapsulated insecticide to give an insecticide concentration in the composition of from 0.001 to 5% w/w;
(b) one or more solvents in an amount of from 1 to 20% w/w;
(c) one or more emulsifiers in an amount of from 0.2 to 10% w/w and selected from the group comprising mono-, di-and tri-sorbitan esters, polyoxyethylene sorbitan esters, mono- and poly-glycerol esters, ethoxylated nonionic emulsifiers, propoxylated nonionic emulsifiers and ethoxylated/propoxylated nonionic emulsifiers;
(d) from 2 to 80% w/w of one or more propellants;
(e) optionally from 0.001 to 5% w/w of one or more oil phase soluble insecticides; and
(f) the balance being water;

the composition having an HLB requirement of 4 to 7, preferably 4.5–6.5, most preferably about 5.5.

Surprisingly, it has been found that in use, the compositions of the invention wherein the microencapsulated insecticide is a synthetic pyrethroid, retain their insecticidal activity when sprayed onto synthetic polymeric surfaces such as vinyl "surfaces". This is unexpected as it has been found in the past that prior art pyrethroid compositions are substantially reduced in their insecticidal activity on vinyl "surfaces".

Accordingly, in a third and related aspect, this invention still further consists in a method of killing insects that contact a synthetic polymeric surface comprising applying to the surface an insecticidal composition in the form of an aerosol water-in-oil emulsion comprising (a) an amount of an aqueous suspension of microencapsulated insecticide to give an insecticide concentration in the composition of from 0.001 to 5% w/w;
(b) one or more solvents in an amount of from 1 to 20% w/w;
(c) one or more emulsifiers in an amount of from 0.2 to 10% w/w and selected from the group comprising mono-di-and tri-sorbitan esters, polyoxyethylene sorbitan esters, mono- and poly-glycerol esters, ethoxylated nonionic emulsifiers, propoxylated nonionic emulsifiers and ethoxylated/propoxylated nonionic emulsifiers;
(d) from 2 to 80% w/w of one or more propellants;
(e) optionally from 0.001 to 5% w/w of one or more oil phase soluble insecticides; and
(f) the balance being water.

Throughout this specification all percentages are w/w unless otherwise stated.

MICROENCAPSULATED INSECTICIDE

The microencapsulated insecticide in incorporated in the compositions of the invention as an aqueous suspension so as to give a concentration of insecticide in a composition of from 0.001 to 5%. A preferred concentration range is from 0.001 to 1%.

A wide range of active insecticides may be used of which pyrethroids, particularly synthetic pyrethroids, chlorpyrifos and diazinon are preferred.

When a synthetic pyrethoid such as imiprothrin is used, generally it will be incorporated in an amount to give a concentration at the lower end of the range, i.e. 0.001% or more.

Synthetic pyrethroids such as lambda cyhalothrin will generally be incorporated in higher concentrations such as 0.01 to 0.5%, preferably 0.01 to 0.1%, most preferably about 0.06%.

Other synthetic pyrethroids such as cypermethrin, permethrin will generally be incorporated to give a concentration of about 0.2% or 0.4% respectively or more.

Chlorpyrifos and diazinon will generally be incorporated to give concentrations in the range of 0.5 to 0.9% or about 0.6% respectively.

For most applications, the preferred concentration of insecticide will be 0.001 to 1%.

A wide range of microencapsulation technologies and compositions may be used, providing that the microencapsulated insecticide is capable of being formed into an aqueous dispersion.

One form of microencapsulation technology that is particularly useful in this invention is that offered by Zeneca and in particular its microencapsulated lambda cyhalothrin is available as DEMAND CS®. This material is made according to EP-A-85301744 and is presented as aqueous suspensions, the concentration of the active insecticide being about 2.5% or 10% w/v. Preferably the 10% w/v material is used in this invention.

DEMAND CS® may be incorporated in the compositions of the present invention to give an insecticide concentration of about 0.06%.

SOLVENT

In order to maintain emulsion stability and where required to enable the incorporation of an optional oil phase soluble insecticide, a solvent is incorporated in the compositions of the invention in an amount of from 1 to 20%. Generally, the solvent will be water immiscible.

A wide range of solvent materials may be used, although care should be exercised to ensure that the solvent does not adversely affect insecticidal activity or effect the microcapsules. Specifically, the solvent selected should not dissolve the microcapsules, nor rupture the walls thereof or cause the insecticide to be discharged by leaching.

Furthermore, it should be noted that combinations of solvents may be used.

Examples of solvents that may be used in the compositions of the invention include:

liquid n-paraffins, liquid isoparaffins, cycloalkanes, naphthene-containing solvents, white spirit, kerosene, ester solvents, silicone solvents or oils, fatty acids, dialkyl phthalates, $C_5$–$C_{11}$ alcohols and fatty alcohols. Specific examples of these are as follows:

liquid n-paraffins-Norpar 12, Norpar 13 and Norpar 15 (available from Exxon)

liquid isoparaffins-Isopar G, Isopar H, Isopar L, Isopar M and Isopar V (available from Exxon)

Naphthene-containing solvents-Exxsol D40, Exxsol D60, Exxsol D80, Exxsol D100, Exxsol D110, Nappar 10 (available from Exxon)

Ester solvents-such as alkyl acetates, examples being Exxate 1000, Exxate 1300 (available from Exxon), and Coasol (available from Chemoxy International);

Silicone solvents oils-Dow Corning 244, 245, 344 and 345 fluids,

Fatty acids—caprylic acid, caproic acid, capric acid, lauric acid, myristic acid, palmatic acid, stearic acid, behenic acid, oleic acid;

Fatty alcohols—octanol, dodecanol, lauryl alcohol, myristyl alcohol, cetyl alcohol, stearyl alcohol, cetostearyl alcohol, oleyl alcohol.

Preferred solvents are liquid hydrocarbon solvents, n-paraffins, and iso-paraffins.

Although the solvent may be incorporated as a level of from 1 to 20%, preferably the concentration will be in the range of 2 to 10%, most preferably about 5%.

PROPELLANTS

One or more propellants are used in the composition of the invention in a total amount of from 2 to 80%. Amongst the propellants that may be used are hydrocarbons and compressed gas of which hydrocarbons are preferred.

In the case of the hydrocarbon propellants those that may be used are acetylene, methane, ethane, ethylene, propane, propene, n-butane, nu-butene, isobutane, isobutene, pentane, pentene, isopentane and isopentene, Mixtures of these propellants may also be used. Indeed, it should be noted that commercially available propellants typically contain a number of hydrocarbon gases. For example, an odorised commercial butane, available from Boral gas contains predominantly n-butane and some iso-butane along with small amounts of propane, propene, pentane and butene.

Preferred hydrocarbon propellants include propane, n-butane, isobutane, pentane and isopentane, whilst most preferred are propane, iso-butane and n-butane.

Particularly preferred hydrocarbon propellants are mixtures of propane, n-butane and iso-butane.

Whilst broadly the concentration of hydrocarbon propellant will be from 2 to 80%, generally the concentration will be from 10 to 60%, preferably 25 to 60% most preferably about 40%.

When compressed gases are used as a propellant generally these will be carbon dioxide, nitrogen or air. Usually, they will be used at a concentration of 2 to 10%, preferably about 5%.

The person skilled in the art will appreciate that the pressure in an aerosol package will be determined by propellant or mixture of propellant. This pressure will have a determining effect on spray rates. Hence for any particular valve system, varying the propellant or propellant mixture will allow for the selection of a desired spray rate.

Likewise for a particular propellant or propellant mixture, it is possible to select a valve and actuator system to achieve a desired rate.

EMULSIFIERS

One or more emulsifiers in an amount of from 0.2 to 10% and selected from the group comprising mono-, di- and tri-sorbitan esters, polyoxyethylene sorbitan esters, mono- and poly-glycerol esters, ethoxylated nonionic emulsifiers, propoxylated nonionic emulsifiers and ethoxylated/propoxylated nonionic emulsifiers are used in the compositions of the invention. Preferably the emulsifiers are selected from this group only.

Amongst the ethoxylated nonionic emulsifiers may be mentioned: ethoxylated alkyl phenols, ethoxylated dialkylphenols, fatty acid ethoxylates, fatty alcohol ethoxylates and fatty amine ethoxylates.

Preferred amongst the ethoxylated nonionic emulsifiers are: soya amine ethoxylates, tallow amine ethoxylates, octadecylamine ethoxylates, nonylphenol ethoxylates and octylphenol ethoxylates.

Amongst the mono-, di- and tri-sorbitan esters, polyoxyethylene sorbitan esters, mono- and poly-glycerol esters, preferably, the emulsifiers will be esters with $C_{10}$–$C_{22}$ fatty acids. Particularly preferred are $C_{12}$–$C_{18}$ fatty acids.

It has been found advantageous to use two emulsifiers in the compositions of the invention. Generally, one of the emulsifiers will be a polyoxyethylene sorbitan ester whilst the second emulsifier will be chosen from either mono-, di- and tri-sorbitan esters and mono- and poly-glycerol esters.

Alternatively, one of the emulsifiers may be a mono-, di- and tri-sorbitan ester whilst the second emulsifier is selected from ethoxylated alkyl phenols, ethoxylated dialkylphenols, fatty acid ethoxylates, fatty alcohol ethoxylates and fatty amine ethoxylates.

Some combinations of emulsifiers that have been found to be effective are sorbitan monooleate with 20 moles of ethylene oxides sorbitan monooleate; and glycerol monooleate with 20 moles of ethylene oxide sorbitan monooleate.

Whilst the total emulsifier concentration may be 0.2 to 10%, generally the concentration will be 0.5 to 8% preferably 1 to 5%, most preferably about 1 to 2%, particularly about 1.2%.

When two emulsifiers are used, usually the ratio of the polyoxyethylene sorbitan ester to mono-, di- and tri-sorbitan esters or mono- and poly-glycerol esters will be from 0.5 to 3:9.5 to 7, preferably 0.5 to 1.5:9.5 to 8.5, most preferably 1.1:8.9.

Alternatively when one of the emulsifiers is selected from ethoxylated alkyl phenols, ethoxylated dialkylphenols, fatty acid ethoxylates, fatty alcohol ethoxylates and fatty amine ethoxylates, the ratio of these emulsifiers to mono-, di- and tri-sorbitan esters will be from 0.5 to 3:16 to 7, preferably 0.5 to 1.5:13 to 8.5, most preferably 0.5 to 1.0:12 to 9.

OPTIONAL INSECTICIDES AND OTHER INGREDIENTS

A wide range of insecticides may be included in the oil phase as required. These include natural pyrethrum, synthetic pyrethroids, chlorpyrifos, diazinon, dichlorvos and propoxur.

In addition to the optional insecticides, synergists such as MGK-264 and piperonyl butoxide may be included for use in conjunction with pyrethroid insecticides.

The persons skilled in the art will also recognise that a perfume may be readily incorporated in the compositions of the invention to satisfy organoleptic requirements.

In addition, other ingredients such as corrosion inhibitors and preservatives may be used as required.

PREPARATION

The compositions of the invention may be prepared by dispersing the microencapsulated insecticide in water. Solvent plus the emulsifier(s) including if required an optional insecticide, is separately prepared. The water phase is added to the solvent phase so as to produce an emulsified concentrate.

The concentrate is then blended with propellant and filled into cans.

Alternatively, the concentrate and the propellant may be filled into cans together.

DETAILED DESCRIPTION OF THE INVENTION

In order to better understand the nature of this invention, a number of examples will now be described.

EXAMPLE

| Ingredient | % w/w Example No 1 |
|---|---|
| Lambda-cyhalothrin 10 | 0.6 |
| Crester 2076 | 0.75 |
| Norpar 13 | 6.1 |
| Water | 42.55 |
| H55 | 50 |
| HLB | 5 |

| Ingredient | % w/w Example No | | | |
|---|---|---|---|---|
| | 2 | 3 | 4 | 5 |
| Lambda-cyhalothrin 10 | 0.6 | 0.6 | 2.4* | 0.6 |
| Span 80 | 0.9 | 0.75 | 0.68 | 0.675 |
| Tween 80 | 0.1 | — | 0.07 | 0.075 |
| Norpar 13 | 5.97 | 6.1 | 5.87 | 6.1 |
| Water | 42.43 | 42.55 | 40.98 | 42.55 |
| H55 | 50 | 50 | 50 | 50 |
| HLB | 5.3 | 4.3 | 5.3 | 5.4 |

| Ingredient | % w/w Example No 6 |
|---|---|
| Lambda-cyhalothrin 10 | 0.6 |
| Cithrol GMO | 0.75 |
| Norpar 13 | 6.1 |
| Water | 42.55 |
| H55 | 50 |
| HLB | 2.8 |

| Ingredient | % w/w Example No 7 |
|---|---|
| Lambda-cyhalothrin 10 | 0.6 |
| Span 60 | 0.67 |
| Tween 80 | 0.08 |
| Norpar 13 | 3.05 |
| Water | 45.6 |
| H55 | 50 |
| HLB | 5.3 |

| Ingredient | % w/w Example No | | | | |
|---|---|---|---|---|---|
| | 8 | 9 | 10 | 11 | 12 |
| Lambda-cyhalothrin 10 | 0.6 | 0.6 | 0.625 | 0.625 | 0.625 |
| Tetramethrin 93.7 | 0.37 | 0.37 | 0.37 | 0.37 | 0.37 |
| Span 80 | 0.675 | — | 0.675 | 0.675 | 0.81 |
| Tween 80 | 0.075 | — | 0.075 | 0.075 | 0.09 |
| Crester 2076 | — | 0.75 | — | — | — |
| Atmos 300 | — | — | — | — | — |
| Isopar G | — | — | 15.708 | 10 | 9.93 |
| Norpar 13 | 5.73 | 5.73 | — | — | — |
| Water | 42.55 | 42.55 | 52.547 | 48.255 | 48.175 |
| H55 | 50 | 50 | 30 | 40 | 40 |
| HLB | 5.3 | 5.0 | 5.3 | 5.3 | 5.4 |

| Ingredient | % w/w Example No | | | |
|---|---|---|---|---|
| | 13 | 14 | 15 | 16 |
| Lambda-cyhalothrin 10 | 0.625 | 0.625 | 0.625 | 0.625 |
| Tetramethrin 93.7 | 0.37 | 0.37 | 0.37 | 0.37 |
| Span 80 | 0.64 | 1.28 | 1.2 | — |
| Tween 80 | 0.11 | 0.22 | 0.3 | 0.3 |
| Atmos 300 | — | — | — | 0.7 |
| Isopar G | 10 | 9.625 | 9.625 | 9.875 |
| Water | 48.255 | 47.88 | 47.88 | 48.13 |

-continued

| | | | | |
|---|---|---|---|---|
| H55 | 40 | 40 | 40 | 40 |
| HLB | 5.9 | 5.9 | 6 | 6.5 |

| Ingredient | % w/w Example No | | | |
|---|---|---|---|---|
| | 17 | 18 | 19 | 20 |
| Lambda-cyhalothrin 10 | 0.625 | 0.625 | 0.625 | 0.645 |
| Tetramethrin 93.7 | 0.37 | 0.37 | 0.37 | 0.38 |
| Span 80 | — | 1.02 | 0.85 | 1.28 |
| Tween 80 | 0.45 | 0.18 | 0.15 | 0.22 |
| Atmos 300 | 1.05 | — | — | — |
| Isopar G | 9.625 | 9.775 | 9.875 | 3.00 |
| Water | 47.88 | 48.03 | 48.13 | 54.475 |
| H40 | — | — | — | 40 |
| H55 | 40 | 40 | 40 | — |
| HLB | 6.5 | 5.4 | 5.9 | 5.9 |

| Ingredient | % w/w Example No | | | |
|---|---|---|---|---|
| | 21 | 22 | 23 | 24 |
| Lambda-cyhalothrin 10 | 0.645 | 0.645 | 0.645 | 0.645 |
| Tetramethrin 93.7 | 0.38 | 0.38 | 0.38 | 0.38 |
| Span 80 | 1.07 | 1.07 | 1.10 | 1.15 |
| Tween 80 | 0.13 | 0.13 | — | — |
| Dow Corning 244 | 5.00 | — | — | — |
| Dow Coming 245 | — | 5.00 | — | — |
| Isopar G | — | — | 5.00 | 5.00 |
| Teric 18M10 | — | — | 0.10 | 0.15 |
| Water | 52.755 | 52.755 | 52.775 | 52.775 |
| H40 | 40 | 40 | 40 | 40 |
| HLB | 5.5 | 5.5 | 5.9 | 5.5 |

| Ingredient | % w/w Example No | | | |
|---|---|---|---|---|
| | 25 | 26 | 27 | 28 |
| Lambda-cyhalothrin 10 | 0.645 | 0.645 | 0.645 | 0.74 |
| Tetramethrin 93.7 | 0.38 | 0.38 | 0.38 | 0.43 |
| Span 80 | 1.07 | — | 1.02 | 1.16 |
| Span 85 | — | 0.9 | — | — |
| Tween 80 | 0.13 | — | — | 0.20 |
| Antarox DM430 | — | 0.3 | 0.18 | — |
| Norpar 13 | — | — | — | — |
| Isopar G | 5.00 | 5.00 | 5.00 | 2.86 |
| Water | 52.755 | 52.755 | 52.755 | 54.61 |
| H55 | — | — | — | — |
| H40 | 40 | 40 | 40 | 40 |
| HLB | 5.5 | 5.5 | 4.8 | 6.5 |

| Ingredient | % w/w Example No | | |
|---|---|---|---|
| | 29 | 30 | 31 |
| Lambda-cyhalothrin 10 | 0.645 | 0.645 | 0.645 |
| Tetramethrin 93.7 | 0.38 | 0.38 | 0.38 |
| Span 80 | 1.07 | 1.1 | 1.10 |
| Teric N15 | 0.13 | — | — |
| Antarox DM430 | — | 0.1 | — |
| Teric N4 | — | — | 0.1 |
| Isopar G | 5.00 | — | 5.00 |
| Water | 52.755 | 52.755 | 52.775 |
| H40 | 40 | 40 | 40 |
| HLB | 6.5 | 5.7 | 5.6 |

*Lambda-cyhalothrin 2.5 used in place of Lambda-cyhalothrin 10.

INGREDIENTS AND AVAILABILITY

| | |
|---|---|
| Span 60 | sorbitan monostearate (ICI) |
| Span 80 | sorbitan monooleate (ICI) |
| Tween 80 | polyoxyethylene (20) sorbitan monooleate (ICI) |
| Atmos 300 | glycerol monooleate (ICI) |
| Cithrol GMO | glycerol monooleate (Croda) |
| Crester 2076 | polyglycerol oleate ester (Croda) |
| Dow Corning 244 | octamethyl tetrasiloxane 95% (Dow Corning) |
| Dow Corning 245 | decamethyl pentasiloxane 95% (Dow Corning) |
| Teric 18M10 | octadecylamine ethoxylate (ICI) |
| Teric N15 | nonylphenol + 15 moles ethylene oxide (ICI) |
| Teric N4 | nonylphenol + 4 moles ethylene oxide (ICI) |
| Span 85 | sorbitan trioleate (ICI) |
| Antarox DM 430 | ethoxylated di-nonylphenol (GAF) |
| Isopar G | liquid isoparaffin (Exxon) |
| Norpar 13 | liquid n-paraffin (Exxon) |
| Lambda-cyhalothrin 10 | DEMAND 10 CS ® (Zeneca) |
| Lambda-cyhalothrin 2.5 | DEMAND 2.5 CS ® (Zeneca) |
| Tetramethrin 93.7 | Tetramethrin 93.7% (Sumitomo) |
| H55 | Propane/butane blend (Boral) |
| H40 | Propane/butane blend (Boral) |

Each of the examples set out above was prepared according to the method previously described.

EFFICACY

In order to demonstrate the efficacy of compositions of the invention, Example 32 was tested as set out below.

| Ingredient | Example 32 % w/w |
|---|---|
| Lambda-cyhalothrin 10 | 0.625 |
| Tetramethrin 93.7 | 0.370 |
| Span 80 | 1.020 |
| Tween 80 | 0.180 |
| Isopar G | 9.775 |
| Water | 48.010 |
| H-40 | 40.00 |
| Butylated hydroxytoluene | 0.020 |

1) Indoor study, evaluating the effect of exposure of the American cockroach to a hardboard surface that had been previously sprayed with Example 32. This was compared with an aerosol containing an equivalent quantity of technical grade lambda-cyhalothrin that had not been encapsulated. This trial demonstrated superior performance of Example 32 against the non-encapsulated composition 24 hours post treatment.

2) Outdoor study against the American cockroach, comparing the efficacy of Example 32 against two existing commercial aerosols, one containing cypermethrin and the other containing cyfluthrin. Assessments (% knockdown and mortality) were over a 3 month period, the test surfaces being unpainted plywood, painted hardboard and unglazed terracotta tiles. The trial demonstrated that Example 32 gave superior knockdown and mortality at all assessment periods and on all surfaces when compared with the two commercial products.

3) Outdoor study against the German cockroach, comparing the efficacy of Example 32 against two existing commercial aerosols, one containing cypermethrin and the other containing cyfluthrin. Assessments (% knockdown and mortality) were over a 3 month period, the test surfaces being unpainted plywood, painted hardboard and unglazed terracotta tiles. The trail demonstrated in Example 32 gave superior knockdown and mortality at all assessment periods and on all surfaces when compared with the two commercial products.

4) Outdoor study against the American cockroach, evaluating the efficacy of Example 32. Knockdown was assessed for up to 3 months post treatment, the test surfaces being terracotta brick, terracotta unglazed tiles, compressed cement sheeting and rough-sawn timber. From this trial it was concluded that Example 32 gave excellent 3 month outdoor residual control of American cockroaches when applied to a variety of typical porous surfaces.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

We claim:

1. An insecticidal composition in the form of an aerosol water-in-oil emulsion comprising:

(a) an amount of an aqueous suspension of microencapsulated pyrethroid insecticide to give an insecticide concentration in the composition of from 0.001 to 5% w/w;

(b) one or more solvents in an amount of from 1 to 20% w/w and selected from the group consisting of liquid n-paraffins, liquid isoparaffins, cycloalkanes, naphthene-containing solvents, white spirit, kerosene, ester solvents, silicone solvents or oils, fatty acids, dialkyl phthalates, $C_5$–$C_{11}$ alcohols and fatty alcohols;

(c) one or more emulsifiers in an amount of from 0.5 to 8% w/w and selected from the group consisting of mono-, di- and tri-sorbitan esters, polyoxyethylene sorbitan esters, mono- and poly-glycerol esters, ethoxylated nonionic emulsifiers, propoxylated nonionic emulsifiers and ethoxylated/propoxylated nonionic emulsifiers;

(d) from 2 to 80% w/w of one or more propellants;

(e) from 0 to 5% w/w of one or more oil phase soluble insecticides; and (f) water sufficient to bring the total composition to 100% w/w.

2. An insecticidal composition as in claim 1 wherein the one or more emulsifiers are selected from the group consisting of mono-, di- and tri-sorbitan esters, polyoxyethylene sorbitan esters, mono- and poly-glycerol esters.

3. An insecticidal composition as in claim 2 including as emulsifiers a polyoxyethylene sorbitan ester and either a mono-, di- or tri-sorbitan ester or a mono- or poly-glycerol ester.

4. An insecticidal composition as in claim 3 wherein the esters are formed with $C_{10}$–$C_{22}$ fatty acids.

5. An insecticidal composition as in claim 4 wherein the esters are formed with $C_{12}$–$C_{18}$ fatty acids.

6. An insecticidal composition as in claim 5 wherein the emulsifiers are 20 moles of ethylene oxide sorbitan monooleate with either sorbitan monooleate or glycerol mono- or poly-oleates.

7. An insecticidal composition of claim 1, wherein the insects are selected from the group consisting of German cockroaches and American cockroaches.

8. An insecticidal composition as in claim 1 wherein the concentration of the one or more emulsifiers is 1 to 5% w/w.

9. An insecticidal composition as in claim 8 wherein the concentration of the one or more emulsifiers is about 1 to 2% w/w.

10. An insecticidal composition as in claim 3 wherein the ratio of polyoxyethylene sorbitan ester to mono-, di- or tri-sorbitan esters or mono- or polyglycerol esters is 0.5 to 3:9.5 to 7.

11. An insecticidal composition as in claim 10 wherein the ratio of polyoxyethylene sorbitan ester to mono-, di- or tri-sorbitan esters or mono- or polyglycerol, esters is 0.5 to 1.5:9.5 to 8.5.

12. An insecticidal composition in the form of an aerosol water-in-oil emulsion comprising:

(a) an amount of an aqueous suspension of microencapsulated pyrethroid insecticide to give an insecticide concentration in the composition of from 0.001 to 5% w/w;

(b) one or more solvents in an amount of from 1 to 20% w/w and selected from the group consisting of liquid n-paraffins, liquid isoparaffins, cycloalkanes, naphthene-containing solvents, white spirit, kerosene, ester solvents, silicone solvents or oils, fatty acids, dialkyl phthalates, $C_5$–$C_{11}$ alcohols and fatty alcohols;

(c) one or more emulsifiers in an amount of from 0.5 to 8% w/w and selected from the group consisting of mono-, di- and tri-sorbitan esters, polyoxyethylene sorbitan esters, mono- and poly-glycerol esters, ethoxylated nonionic emulsifiers, propoxylated nonionic emulsifiers and ethoxylated/propoxylated nonionic emulsifiers;

(d) from 2 to 80% w/w of one or more propellants;

(e) from 0 to 5% w/w of one or more oil phase soluble insecticides; and (f) water sufficient to bring the total composition to 100% w/w, the composition having an HLB requirement of 4 to 7.

13. An insecticidal composition as in claim 12 wherein the composition has an HLB requirement of 4.5–6.5.

14. An insecticidal composition as in claim 13 wherein the composition has an HLB requirement of about 5.5.

15. An insecticidal composition as in claim 1, wherein the emulsifier is selected from the group consisting of ethoxylated nonionic emulsifiers, propoxylated nonionic emulsifiers, ethoxylated/propoxylated nonionic emulsifiers and mono-, di- or tri-sorbitan esters.

16. An insecticidal composition as in claim 15, wherein the emulsifier is selected from the group consisting of ethoxylated alkyl phenols, ethoxylated dialkylphenols, fatty acid ethoxylates, fatty alcohol ethoxylates and fatty amine ethoxylates.

17. An insecticidal composition as in claim 16, wherein the emulsifier is selected from soya amine ethoxylates, tallow amine ethoxylates, octadecylamine ethoxylates, nonylphenol ethoxylates and octylphenol ethoxylates.

18. An insecticidal composition as in claim 15 including as emulsifiers a mono-, di- or tri-sorbitan ester and one of ethoxylated nonionic emulsifiers, propoxylated nonionic emulsifiers, ethoxylated/propoxylated nonionic emulsifiers.

19. An insecticidal composition as in claim 18 including as emulsifiers a mono-, di- or tri-sorbitan ester and one of ethoxylated alkyl phenols, ethoxylated dialkylphenols, fatty acid ethoxylates, fatty alcohol ethoxylates and fatty amine ethoxylates.

20. An insecticidal composition as in claim 19 wherein the ratio of ethoxylated alkyl phenols, ethoxylated dialkylphenols, fatty acid ethoxylates, fatty alcohol ethoxylates and fatty amine ethoxylates to mono-, di- and tri-sorbitan esters is 0.5 to 3:16 to 7.

21. An insecticidal composition as in claim 20 wherein the ratio of ethoxylated alkyl phenols, ethoxylated dialkylphenols, fatty acid ethoxylates, fatty alcohol ethoxylates and fatty amine ethoxylates to mono-, di- and tri-sorbitan esters is 0.5 to 1.5:13 to 8.5.

22. An insecticidal composition as in claim 21 wherein the ratio of ethoxylated alkyl phenols, ethoxylated dialkylphenols, fatty acid ethoxylates, fatty alcohol ethoxylates and fatty amine ethoxylates to mono-, di- and tri-sorbitan esters is 0.5 to 1.0:12 to 9.

23. An insecticidal composition as in claim 19 including as emulsifiers a mono-, di- or tri-sorbitan ester and one of soya amine ethoxylates, tallow amine ethoxylates, octadecylamine ethoxylates, nonylphenol ethoxylates and octylphenol ethoxylates.

24. An insecticidal composition as in claim 1 wherein the concentration of microencapsulated insecticide is from 0.001 to 1% w/w.

25. An insecticidal composition as in claim 24 wherein the insecticide is lambda cyhalothrin in a concentration of 0.01 to 0.5% w/w.

26. An insecticidal composition as in claim 25 wherein the lambda cyhalothrin is in a concentration of 0.01 to 0.1% w/w.

27. An insecticidal composition as in claim 26 wherein the lambda cyhalothrin is in a concentration of about 0.06% w/w.

28. An insecticidal composition as in claim 1 wherein the concentration of solvent is from 2 to 10% w/w.

29. An insecticidal composition as in claim 28 wherein the concentration of solvent is about 5% w/w.

30. An insecticidal composition as in claim 1 wherein the propellant comprises a mixture of hydrocarbons, in a concentration of from 10 to 60% w/w.

31. An insecticidal composition as in claim 30 wherein the propellant comprises a mixture of hydrocarbons, in a concentration of from 25 to 60% w/w.

32. An insecticidal composition as in claim 31 wherein the propellant comprises a mixture of hydrocarbons, in a concentration of about 40%.

33. An insecticidal composition as claimed in claim 30 wherein the propellant is a mixture of propane, n-butane and iso-butane.

34. An insecticidal composition as in claim 1 wherein the propellant is a compressed gas in a concentration of from 2 to 10% w/w.

35. An insecticidal composition as in claim 34 wherein the propellant is a compressed gas in a concentration of about 5% w/w.

36. An insecticidal composition as in claim 1 including an oil phase soluble insecticide.

37. An insecticidal composition as in claim 1 wherein the solvents are selected from the group consisting of liquid hydrocarbon solvents, n-paraffins and isoparaffins.

38. A method of killing insects that contact a synthetic polymeric surface comprising applying to the surface an insecticidal composition in the form of an aerosol water-in-oil emulsion, said composition comprising:

(a) an amount of an aqueous suspension of microencapsulated pyrethroid insecticide to give an insecticide concentration in the composition of from 0.001 to 5% w/w;

(b) one or more solvents in an amount of from 1 to 20% w/w and selected from the group consisting of liquid n-paraffins, liquid isoparaffins, cycloalkanes, naphthene-containing solvents, white spirit, kerosene, ester solvents, silicone solvents or oils, fatty acids, dialkyl phthalates, $C_5$–$C_{11}$ alcohols and fatty alcohols;

(c) one or more emulsifiers in an amount of from 0.5 to 8% w/w and selected from the group consisting of mono-, di- and tri-sorbitan esters, polyoxyethylene sorbitan esters, mono- and poly-glycerol esters, ethoxylated nonionic emulsifiers, propoxylated nonionic emulsifiers and ethoxylated/propoxylated nonionic emulsifiers;

(d) from 2 to 80% w/w of one or more propellants;

(e) from 0 to 5% w/w of one or more oil phase soluble insecticides; and (f) water sufficient to bring the total composition to 100% w/w.

39. A method of killing insects according to claim 38, wherein the insects are selected from the group consisting of German cockroaches and American cockroaches.

* * * * *